(12) United States Patent
Scott et al.

(10) Patent No.: US 8,598,165 B2
(45) Date of Patent: Dec. 3, 2013

(54) MORPHOLINES AS SELECTIVE INHIBITORS OF CYTOCHROME P450 2A13

(75) Inventors: Emily Scott, Lawrence, KS (US); Anuradha Roy, Kansas City, MO (US)

(73) Assignee: University of Kansas, Lawrence, KS (US)

( * ) Notice: Subject to any disclaimer, the term of this patent is extended or adjusted under 35 U.S.C. 154(b) by 885 days.

(21) Appl. No.: 12/277,097

(22) Filed: Nov. 24, 2008

(65) Prior Publication Data

US 2009/0137592 A1    May 28, 2009

Related U.S. Application Data

(60) Provisional application No. 60/990,248, filed on Nov. 26, 2007.

(51) Int. Cl.
*C07D 265/30* (2006.01)

(52) U.S. Cl.
USPC ........................................ 514/231.2; 544/106

(58) Field of Classification Search
None
See application file for complete search history.

(56) References Cited

U.S. PATENT DOCUMENTS

| | | | |
|---|---|---|---|
| 4,107,288 | A | 8/1978 | Oppenheim et al. |
| 5,013,556 | A | 5/1991 | Woodle et al. |
| 5,145,684 | A | 9/1992 | Liversidge et al. |
| 5,879,713 | A | 3/1999 | Roth et al. |
| 5,954,061 | A | 9/1999 | Cardarelli |
| 6,233,488 | B1 | 5/2001 | Hess |
| 6,333,357 | B1 | 12/2001 | Eig |
| 6,559,768 | B2 | 5/2003 | Schaffner et al. |
| 6,596,740 | B2 | 7/2003 | Jones |
| 6,845,777 | B2 | 1/2005 | Pera |
| 2006/0160800 | A1 | 7/2006 | Hangauer |

FOREIGN PATENT DOCUMENTS

| | | | |
|---|---|---|---|
| FR | M4162 | * | 6/1966 |
| WO | WO 2005/066162 | | 7/2005 |
| WO | WO 2006/015123 | | 2/2006 |
| WO | WO 2006/071960 | | 7/2006 |
| WO | WO 2006/108149 | | 10/2006 |
| WO | WO 2005/077912 | | 8/2008 |

OTHER PUBLICATIONS

Haber, Texas Occupational Medicine Institute, "Lung Carcinogens", Jun. 2004, downloaded on Dec. 16, 2011 from "https://tomi-md.com/2009/06/lung-carcinogens/", pp. 1-2 of 2.*
Hecht, Journal of the National Cancer Institute, "Tobacco Smoke Carcinogens and Lung Cancer", 7/199, vol. 91(14), pp. 1994-1210.*
Magerramov et al., Russian Journal of Applied Chemistry, "Synthesis of N-Substituted Oxazolidines and Morpholines", 2005, vol. 78(8), pp. 1301-1305.*
Database Registry [Online] Chemical Abstracts Service, Columbus, Ohio, US; 1984, XP002613570, Database Accession No. 51180-64-4.
Database Registry [Online] Chemical Abstracts Service, Columbus, Ohio, US; 1984, XP002613571, Database Accession N. 416892-44-9.
Database Registry [Online] Chemical Abstracts Service, Columbus, Ohio, US; , XP002613572, Database Accession n. 415932-72-8.
Von Weymarn, Linda B et al: "Effects of 8-methoxypsoralen on cytochrome P450 2A13." Mar. 2005, Carcinogenesis Mar. 2005 LNKD—PUBMED: 15579482, vol. 26, NR. 3, pp. 621-629, XP002613573, ISSN: 0143-3334.
Von Weymarn, Linda B et al: "Effects of benzyl and phenethyl isothiocyanate on P450s 2A6 and 2A13: potential for chemoprevention in smokers", Carcinogenesis, Oxford University Press, GB, vol. 27, No. 4, Jan. 1, 2006, pp. 782-790, XP00250505082; ISSN: 0143-3334, DOI: DOI:10.1093/CARCIN/BGI301 [retrieved on Dec. 19, 2005].
Drug Metabolism and Disposition. LNKD—PUBMED:16815959, vol. 34, No. 10, Oct. 2006, pp. 1672-1676, XP002613574, ISSN: 0090-9556, Zhu et al.
Devore, N M et al, "Key residues controlling binding of diverse ligands to human cytochrome P450 2A enzymes.", Drug Metabolism and Disposition: LNKD—PUBMED:19251817, vol. 37, No. 6, Jun. 2009, pp. 1319-1327, XP002613575, ISSN: 1521-009X.
Supplemental European Search Report dated Dec. 22, 2010 as issued in connection with corresponding European Application No. 08854203.0, filed on Jun. 25, 2010.
Brough, P. A., et al.; 4,5-Diarylisoxazole Hsp90 Chaperone Inhibitors: Potential Therapeutic Agents for the Treatment of Cancer, Journal of Medicinal Chemistry, 2008, pp. 196-218, vol. 51, No. 2, American Chemical Society, US.
Scott, E. E., et al.; An Open Conformation of Mammalian Cytochrome P450 2B4 at 1.6-Å Resolution; Proceedings of the National Academy of Sciences of the United States of America (PNAS); Nov. 11, 2003; pp. 13196-13201; vol. 100, No. 23; USA.
Smith, B. D. et al.; Structure of the Human Lung Cytochrome P450 2A13; Journal of Biological Chemistry; Jun. 8, 2007; pp. 17306-17313; vol. 282, No. 23; The American Society for Biochemistry and Molecular Biology, Inc.; USA.

* cited by examiner

*Primary Examiner* — Melenie McCormick
*Assistant Examiner* — Gregg Polansky
(74) *Attorney, Agent, or Firm* — Licata & Tyrrell, P.C.

(57) ABSTRACT

A method of inhibiting formation of cancerous metabolites, of inhibiting cytochrome P450 2A13 from forming carcinogen metabolites, and/or inhibiting formation of cancerous lung cells in a subject can include: providing a morpholine compound that selectively interacts with cytochrome P450 2A13 over cytochrome P450 2A6; administering a therapeutically effective amount of the morpholine compound or derivative to the subject. The morpholine compound or derivative can be substantially more selective for interacting with the cytochrome P450 2A13 over the cytochrome P450 2A6. The morpholine compound or derivative can also be substantially non-interactive with other physiological components. The morpholine compound or derivative can include a structure that selectively interacts with cytochrome P450 2A13 over cytochrome P450 2A6, such as Compounds 1-34 of Formulas A-D.

5 Claims, 5 Drawing Sheets

MORPHOLINES AS SELECTIVE INHIBITORS OF CYTOCHROME P450 2A13

CROSS-REFERENCE TO RELATED APPLICATIONS

This patent application claims benefit of U.S. patent application Ser. No. 60/990,248, filed Nov. 26, 2007, which provisional application is incorporated herein by specific reference in its entirety.

This invention was made with government support under grant number GM076343 awarded by the National Institutes for Health. The government has certain rights in the invention.

BACKGROUND OF THE INVENTION

In 2003, the Centers for Disease Control and Prevention estimated that approximately 25.5 million men and 21.5 million women smoke. In other words, 24.1% of all men and 19.2% of all women are smokers. There are many reasons people start smoking, including, but not limited to, stress, life problems, peer pressure, family history, and personality tendencies. There are also many reasons people to want to quit smoking, including, but not limited to, health problems (such as lung cancer); and the smell, stained teeth, bad breath, wrinkled skin, and yellow nails associated with smoking. Moreover, smoking can cause the average male to lose 13.2 years of his life, and the average female to lose 14.5 years of her life.

People have invented many ways to quit smoking. U.S. Pat. No. 6,845,777 to Pera (2005) employs a composition that can take a capsule, powder, or liquid form, and that satisfies a smoker's craving for nicotine. U.S. Pat. No. 6,596,740 to Jones (2003) satisfies a smoker's craving for nicotine via a nasal spray. Other "quit smoking" inventions include, but are not limited to, adult pacifiers (i.e., U.S. Pat. No. 6,458,159 to Peters-Combs (2002)); cigarette aeration and filtration devices (i.e., U.S. Pat. No. 5,954,061 (1999)); wristwatches (i.e., U.S. Pat. No. 6,305,939 to Krstulovic (2001)); spinal cord stimulation (i.e., U.S. Pat. No. 6,233,488 to Hess (2001)); and chemotherapy (i.e., U.S. Pat. No. 6,333,357 to Eig (2001)). There is even a cigarette pack that plays an anti-smoking message each time the smoker opens it (U.S. Pat. No. 6,559,768 to Schaffner, et al. (2003)).

Despite all the creative ways people have tried to quit smoking, a study by the American Cancer Society in 2005 shows that only 2.5% of smokers who try to quit smoking each year actually succeed. Clearly, there is still a need for more ways to quit smoking; for, not every method will work for each individual smoker.

However, there also is a need for inhibiting the physiological effects of smoking for individuals who cannot quit or have a difficult and/or prolonged program to stop smoking. Thus, it can be advantageous to treat, inhibit, or prevent the adverse physiological effects of smoking so that the overall health of a smoker is maintained or increased.

SUMMARY

In one embodiment, the present invention includes a method of inhibiting formation of cancerous metabolites in a subject. Such a method can include: providing a morpholine compound that selectively interacts with cytochrome P450 2A13 over cytochrome P450 2A6; administering a therapeutically effective amount of the morpholine compound to the subject so as to inhibit formation of the cancerous metabolites by the cytochrome P450 2A13. The morpholine compound can be substantially more selective for interacting with the cytochrome P450 2A13 over the cytochrome P450 2A6. The morpholine compound can also be substantially non-interactive with other physiological components.

In one embodiment, the present invention can include a method of inhibiting formation of cancerous lung cells in a subject. Such a method can include: providing a morpholine compound that selectively interacts with cytochrome P450 2A13 over cytochrome P450 2A6; and administering a therapeutically effective amount of the morpholine compound to the subject so as to inhibit formation of the cancerous lung cells.

In one embodiment, the present invention can include a method of inhibiting cytochrome P450 2A13 from forming carcinogen metabolites in a subject. Such a method can include: providing a morpholine compound that selectively interacts with cytochrome P450 2A13 over cytochrome P450 2A6; and administering a therapeutically effective amount of the morpholine compound to the subject so as to inhibit cytochrome P450 2A13 from interacting with 4-(methylnitrosamino)-1-(3-pyridyl)-1-butanone (NNK).

In one embodiment, the present invention can include a morpholine compound that inhibits formation of cancerous metabolites in a subject. Such a morpholine compound can include a structure that selectively interacts with cytochrome P450 2A13 over cytochrome P450 2A6.

In one embodiment, the morpholine compound can be selected from Compounds 1-34, more preferably 1-10.

In one embodiment, the morpholine compound can be selected from Formulas A-D.

In one embodiment, the morpholine compound can be included in pharmaceutically acceptable carrier in a therapeutically effective amount.

These and other embodiments and features of the present invention will become more fully apparent from the following description and appended claims, or may be learned by the practice of the invention as set forth hereinafter.

FIGURES

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

Figure 1A:
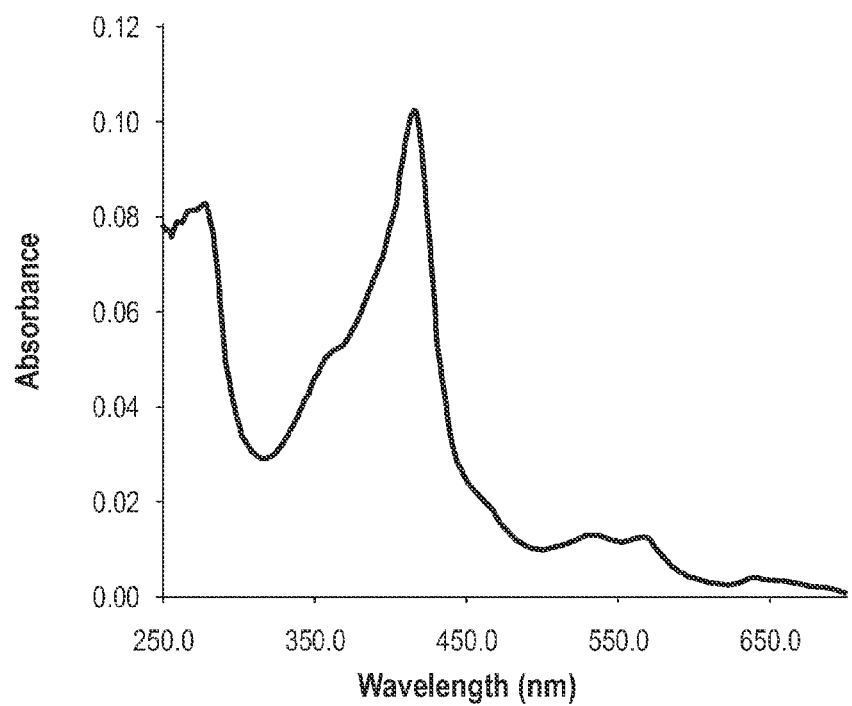
FIG. 1A is a graph illustrating the UV/visible spectrum of purified CYP2A protein, which shows a Soret peak at 418 nm, indicative of a low-spin, six-coordinate configuration of the heme iron bound to an active site water molecule.
Figure 1B:
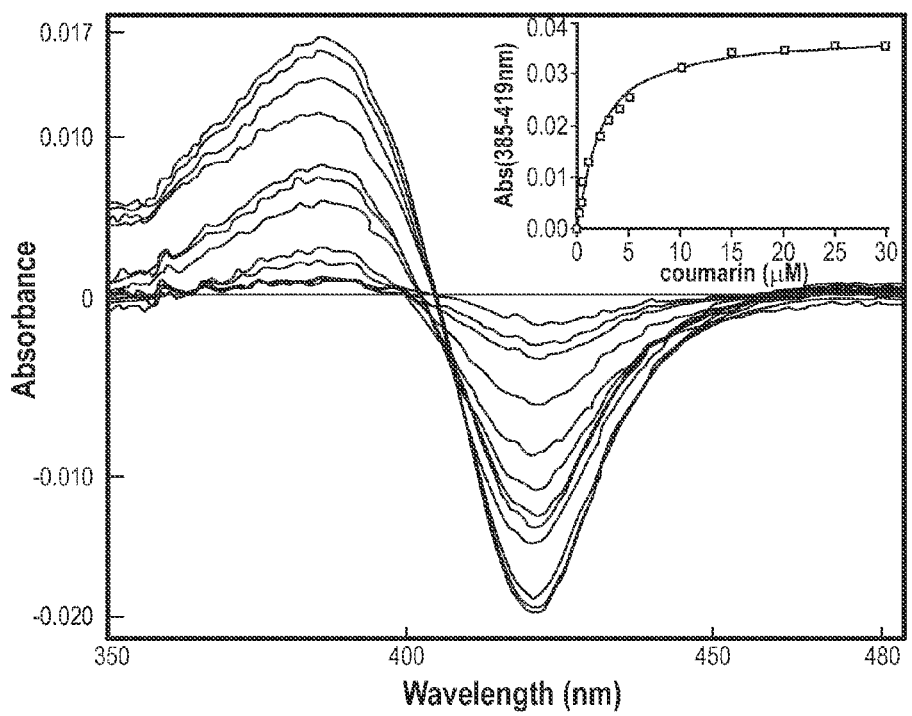
FIG. 1B is a plot illustrating the spectrum shift of cytochrome P450 enzymes that occurs as protein is titrated with increasing concentrations of a ligand and the heme-bound water is displaced. The inset shows how the changes in absorbance are plotted vs. ligand concentration (in this case coumarin) and used to determine ligand affinity ($k_d$) values.
Figure 2:
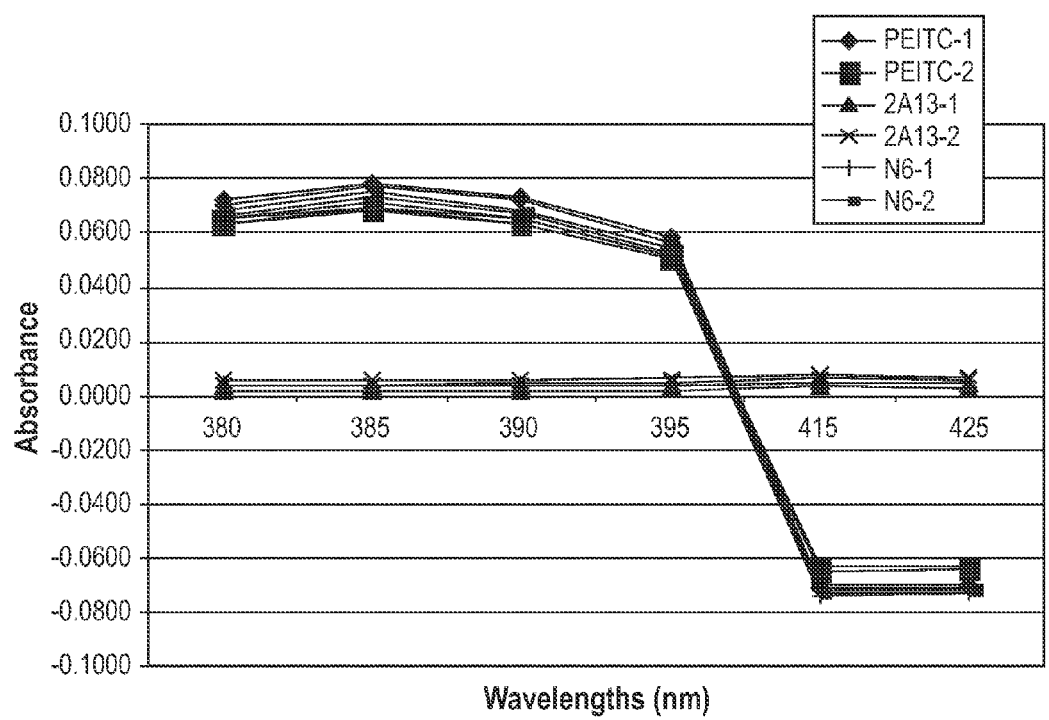

FIG. 2 is a graph illustrating validation of the HTS version of the spectral binding assay in FIG. 1B. This assay uses only six wavelengths for single concentrations of different ligands. This example shows binding of PEITC, a positive control that binds CYP2A13; a negative control (2A13-1 and 2A13-2); and two new compounds identified to bind CYP2A13 (N6-1 and N6-2).

Figure 3A:
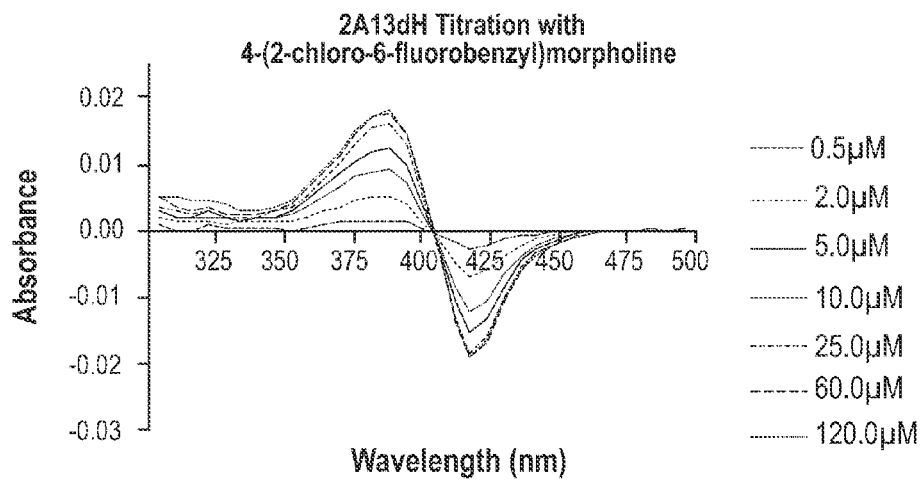

FIG. 3A is a graph that illustrates titration with CYP2A13 reveals binding of 4-(2-chloro-6-fluorobenzyl)morpholine to CYP2A enzymes.

Figure 3B:
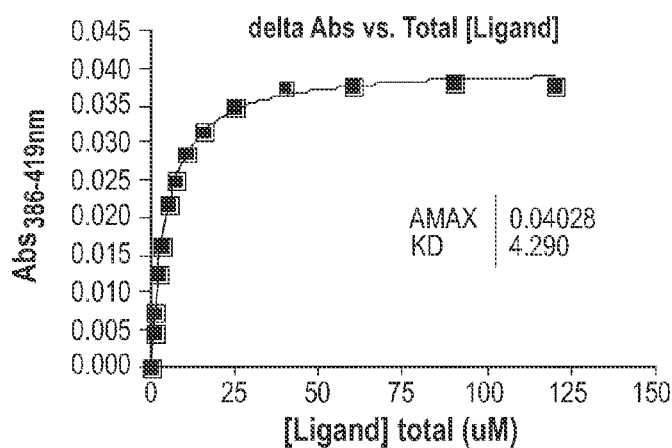

FIG. 3B is a graph that is used to determine 2A13 Kd from data in 3A. Multiple titrations reveal an average Kd of 5.8 mM.

Figure 3C:
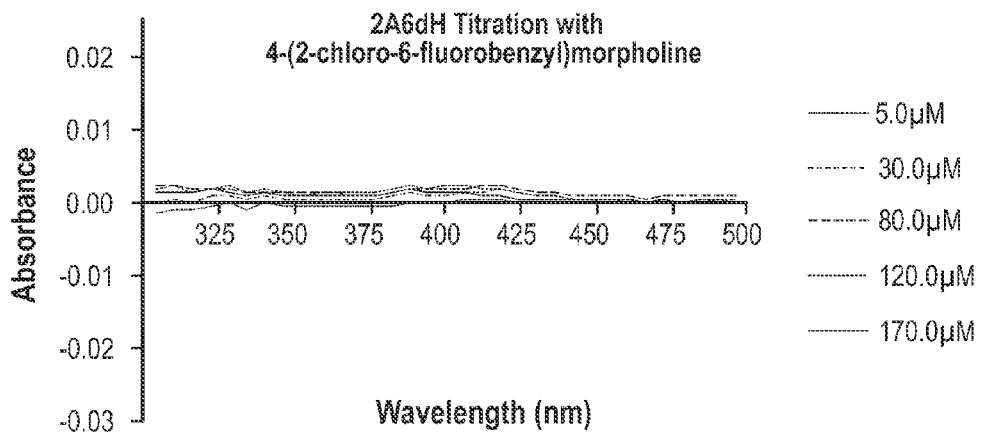

FIG. 3C is a graph that illustrates that titration with CYP2A6 reveals no

Figure 4A:
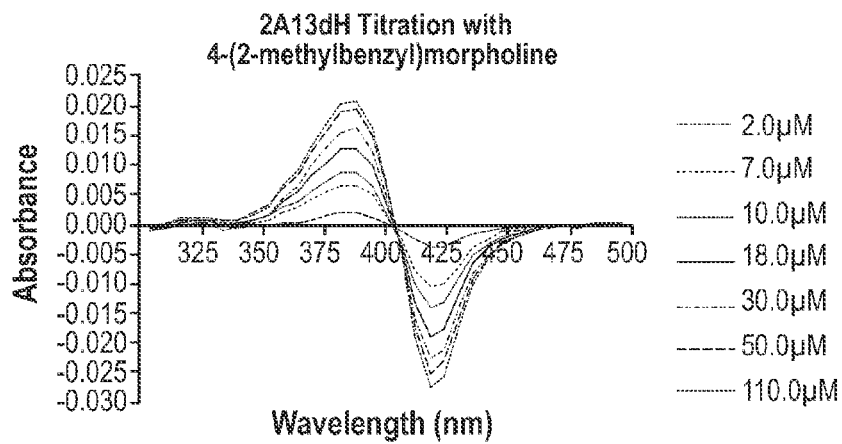

FIG. 4A is a graph that illustrates titration with CYP2A13 reveals binding of 4-(2-methylbenzyl)morpholine to CYP2A enzymes.

Figure 4B:
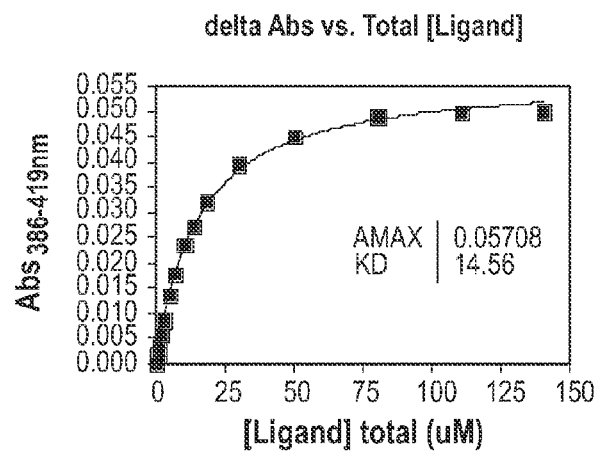

FIG. 4B is a graph that is used to determine 2A13 Kd from data in 4A. Multiple titrations reveal an average Kd of 19.3 µM.

Figure 4C:
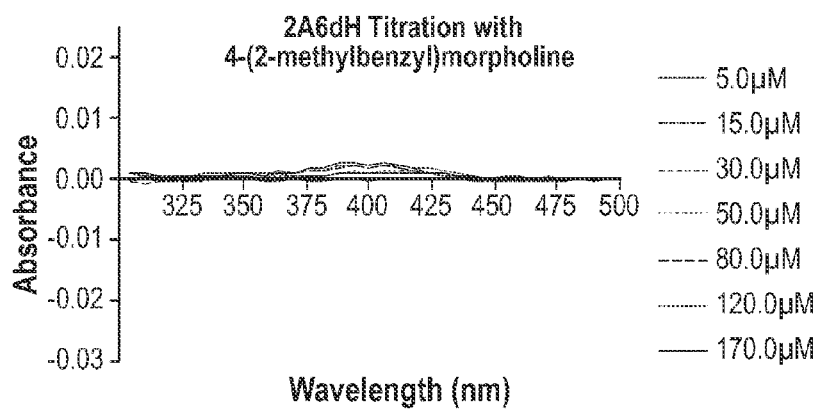

FIG. 4C is a graph that illustrates that titration with CYP2A6 reveals no binding.

Figure 5A:
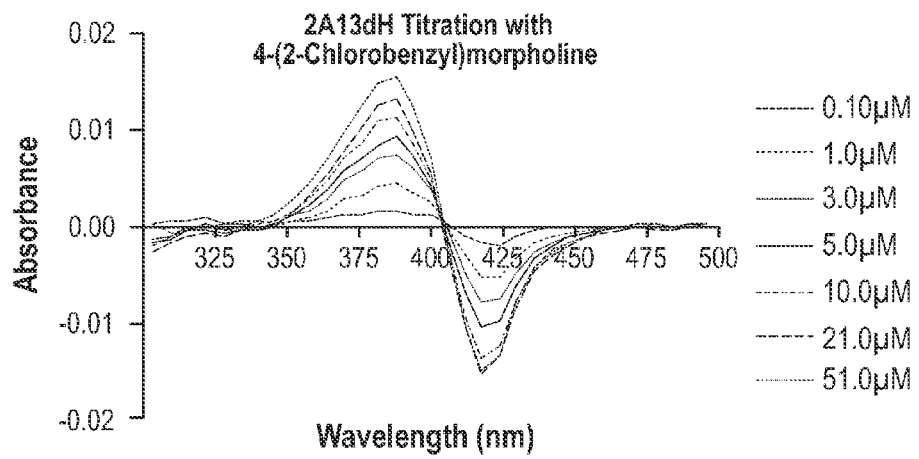

FIG. 5A is a graph that illustrates titration with CYP2A13 reveals binding of 4-(2-chlorobenzyl)morpholine to CYP2A enzymes.

Figure 5B:
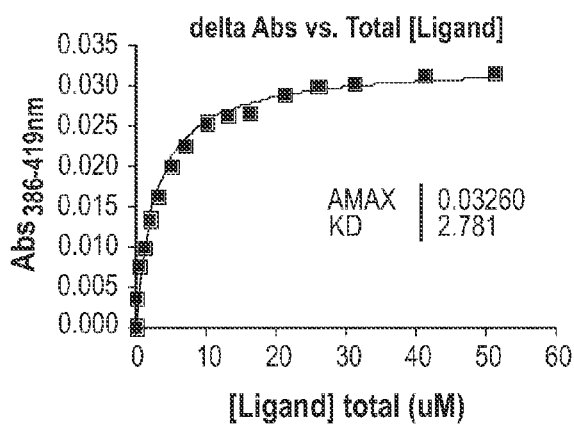

FIG. 5B is a graph that is used to determine 2A13 Kd from data in 5A. Multiple titrations reveal an average Kd of 7.3 mM.

Figure 5C:
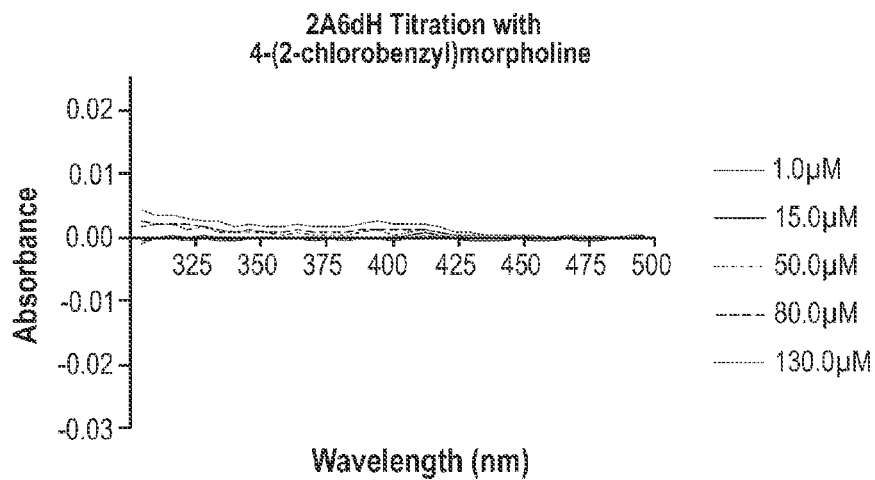

FIG. 5C is a graph that illustrates that titration with CYP2A6 reveals no binding.

DETAILED DESCRIPTION

Lung cancer is a leading cause of human mortality, and smoking is the most critical factor in the development of 80-90% of lung cancer (*Proc Natl Acad Sci USA*. 2004 Jul. 6; 101(27): 10143-10148). The human xenobiotic cytochrome P450 2A13 (CYP2A13), which is mainly expressed in the respiratory tract, efficiently catalyzes metabolism of the tobacco-smoke procarcinogen 4-(methylnitrosamino)-1-(3-pyridyl)-1-butanone (NNK) into two toxic metabolites that intercalate DNA and cause lung cancer in smokers. NNK is one of the most prevalent compounds in cigarette smoke and one of the strongest procarcinogens. As such, the function of CYP2A13 has a significant role in the formation of toxic metabolites that function as carcinogens. These carcinogens can induce the formation of any cancer, but are highly likely to be involved in lung cancer. One method of inhibiting the formation of the carcinogens would be to block the activity of CYP2A13. However, CYP2A13 is 93.5% identical to the human liver drug-metabolizing cytochrome P450 2A6 (CYP2A6), which only metabolizes NNK very inefficiently. As such, a molecule that inhibits CYP2A13 activity may also block CYP2A6 activity, which is undesirable. To overcome the problem associated with similarity of the enzymes, specificity for CYP2A13 over CYP2A6 (and other P450s) can be a factor in identifying an inhibitor for CYP2A13. An inhibitor that selectively inhibits human CYP2A13 over other cytochrome P450 enzymes, but especially CYP2A6, can be used to prevent in vivo generation of the NNK metabolites that cause lung cancer or other cancers in smokers.

I. Inhibiting CYP2A13

The inhibition of CYP2A13 represents an innovative approach to prevention of lung cancer. While many smoking intervention approaches try to alter smoker behavior, replace nicotine delivery, or act at nicotinic receptors to reduce the physiological rewards of smoking, the inhibition of CYP2A13 is an entirely new approach that inhibits the formation of toxic carcinogens that cause lung cancer without requiring alteration of nicotine exposure. Thus, this strategy aims to reduce the risk of developing lung cancer for smokers or those exposed to second hand smoke.

To identify potential inhibitors of CYP2A13, a spectral ligand binding assay was used in a high throughput format to screen a large number of molecules. Confirmation of hits (e.g., molecules that interact with CYP2A13) in a binding titration assay can be used to identify specific molecules or molecule families with similar core scaffolds. This strategy has led to the identification of at least two molecular morpholine-based scaffolds (e.g., genus) that have many different specific scaffold derivatives (e.g., morpholine derivative species molecules) that bind specifically to CYP2A13, but showed little or no binding to the close homolog, CYP2A6. This high selectivity of CYPA13 over CYP2A6 is desirable, and such molecules can be used in the therapeutic protocols described herein.

Preliminary studies indicate that some of the molecules based on these scaffolds also inhibit enzymatic metabolism of CYP2A13 substrates. That is, the molecules not only bind CYP2A13 selectively, but in doing so also inhibit the general function of CYP2A13. Optimal drug candidates have specific interactions as inhibitors of CYP2A13, but not CYP2A6. The identification of selective inhibitors of CYP2A13 can be used to provide more effective drugs with higher functionality and selectivity, and also can be used in lung cancer chemoprevention. Selective drug candidates can target reduction in the in vivo formation of nicotine-derived carcinogens without requiring changes in smoking habits, which may decrease disease. This approach, alone or in combination with existing therapies, can help reduce the incidence of lung cancer. Also, this approach can be used for individual that are trying to quite smoking.

In one embodiment, the present invention can include the use of one or more of a series of morpholine derivatives for inhibiting the formation of the carcinogens, and thereby inhibiting the formation of cancer, such as lung cancer. The morpholine derivatives can be molecules that are available commercially, analogs of commercially available compounds, or new compounds that are synthesized de novo based on the scaffolds presented herein. The morpholine derivatives in accordance with the present invention are selective inhibitors of the enzyme CYP2A13 over CYP2A6. It is preferred that the compound has high selectivity for CYP2A13 versus CYP2A6. A selectivity constant that is essentially a ratio of inhibition of CYP2A13-over inhibition of CYP2A6 can be identified to characterize a potential inhibitor. Thus, the selectivity constant provides as high a ratio of 2A13/2A6 inhibition as possible.

Previously known inhibitors of cytochromes P450 2A enzymes include isothiocyanates (e.g., —N=C=S). The morpholine scaffolds of the present invention have not been previously identified as P450 inhibitors in general or specifically as 2A13-selective inhibitors. Since the isothiocyanates are highly reactive and potentially toxic, they are not suitable drug compounds. The morpholine scaffolds are devoid of isothiocyanate motifs. While some of the morpholine derivatives may be commercially available for other uses, the method of use of such morpholine derivatives for inhibiting CYP2A13 is novel. These morpholines have the potential to inhibit cytochrome CYP2A13 activity in human tissue, such as lung tissue, to prevent the conversion of the nicotine-derived nitrosamine 4-(methylnitrosamino)-1-(3-pyridyl)-1-butanone (NNK) into the two carcinogenic compounds (e.g., Carcinogen A and Carcinogen B) that cause the DNA damage that can initiate lung cancer. The selectivity of the morpholine derivative compounds for CYP2A13 over the closely related human liver CYP2A6 allows for normal liver activity.

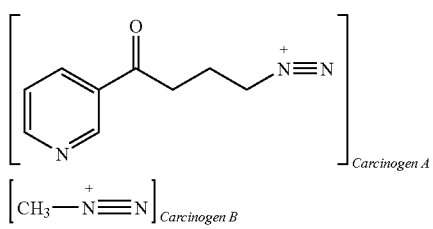

The morpholine compounds can be used as lung cancer chemopreventatives. As chemopreventatives, the morpholine compounds can be used to reduce the risk of lung cancer either in smokers that use nicotine or in people exposed to second-hand smoke. Prevention of lung cancer is an important objective because lung cancer is a leading cause of human mortality. Smoking is the most critical factor in the development of lung cancer, but many smokers either cannot or will not give up nicotine exposure. Also, while trying to stop smoking, many smokers use nicotine gum. As such, inhibition of CYP2A13 can also be used along with nicotine gum to help maintain health during a stressful period and inhibit the formation of carcinogens. Thus, the inhibition of CYP2A13 can be used in smokers, and other people susceptible to the intake of cigarette toxins, such as smokers that are trying to curb their nicotine addiction.

II. Morpholines

Morpholines in accordance with the present invention have been shown to have selectivity for CYP2A13 over CYP2A6. The morpholines screened, as shown below, are candidates for derivatization. As such, the morpholine compounds shown in Tables 1 and 2 below can be prepared into analogues that have modulated potency, selectivity, and solubility in order to provide useful leads for drug discovery and drug development. During optimization, new analogues can be designed considering issues of drug delivery, metabolism, novelty, and safety. The information obtained from the compounds of Tables 1 and 2 was used in order to design additional morpholines that have selectivity for CYP2A13.

Additionally, any of the compounds of Compounds I-34 can be derivatized/analogued as is well known in the art of combinatorial and medicinal chemistry. The analogs or derivatives can be prepared by adding and/or substituting functional groups at various locations on any of compounds of Compounds I-34. As such, the compounds of Compounds I-34 can be converted into derivatives/analogues using well known chemical synthesis procedures. For example, all of the hydrogen atoms or substituents can be selectively modified to generate new analogues. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog", "analogue," or "derivative" is meant to refer to a chemical compound or molecule made from a parent compound or molecule by one or more chemical reactions. As such, an analog can be a compound with a structure similar to that of Compounds I-34 or based on a scaffold of Compounds 1-34, but differing from it in respect to certain components or structural makeup, which may have a similar or opposite action metabolically. An analog or derivative of any of Compounds 1-34 in accordance with the present invention can be used to selectively inhibit CYP2A13.

In one embodiment, the compounds of Compounds 1-34 can independently be derivatized/analogued by modifying hydrogen groups independently from each other into other substituents. That is, each atom on each molecule can be independently modified with respect to the other atoms on the same molecule. Any traditional modification for producing a derivative/analogue can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

In one embodiment, the morpholine compounds can be described by the chemical structures of Formulas A-D, salt thereof, or prodrug thereof.

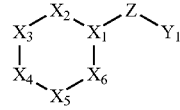

Formula A

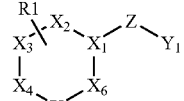

Formula B

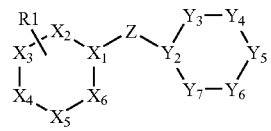

Formula C

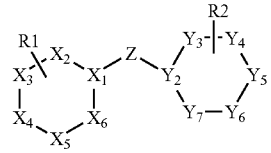

Formula D

In Formula A: $X_{1-6}$ are independently selected from C, N, NH, N-alkyl, O, or S so long as to form a morpholine or morpholine derivative (e.g., thiomorpholines and piperazines are considered to be morpholine derivatives); Z is a linker such as an alkyl, amide, amine, carboxyl, ketone, ester, imine, urea, thiourea, or thioamide functional group (either constitutional isomer, where possible); and $Y_1$ is a substituted or unsubstituted straight chain or branched aliphatic (e.g., C1-C10), an adamantyl (e.g., 2-adamantyl or adamantane derivative), or cycle or heterocycle selected from phenyl, pyridine, pyrimidine, pyrazine, 1,3,5-triazine, 1,2,4-triazine, quinoline, isoquinoline, acridine, phenanthrolines, benzoquinolines, phenathridines, phenazines, quinoxalines, quinazolines, phthalazines, pteridines, cinnolines, pyrroles, imidazoles, 1,2,3-triazoles, 1,2,4, triazoles, tetrazoles, isoxazoles, 1,3-thiazoles, benzimidazoles, indoles, indazoles, benzothiazoles, phenols, naphthols, 2-furan, 3-furan, 2-thiophene, 3-thiophene, 2-pyrrole, 3-pyrrole, 2-oxazole, 4-oxazole, 5-oxazole, 2-thiazole, 4-thiazole, 5-thiazole, 2-imidazole, 4-imidazole, 5-imidazole, 3-isoxazole, 4-isoxazole, 5-isoxazole, 3-isothiazole, 4-isothiazole, 5-isothiazole, 4-(1,2,3) oxadiazole, 5-(1,2,3) oxadiazole, 4-(1,2,3) triazole, 5-(1,2,3) triazole, or 2-(1,3,4) thiadiazole; and n=0, 1, 2, or 3; where the substituted cycle or heterocycle is substituted at any position with H, a halogen, Cl, F, $CH_3$, $CH_3CH_2$, or higher or lower substituted or unsubstituted straight chain or branched aliphatic. The first ring of a morpholine includes $X_{1-6}$, and $Y_1$ can be a second ring.

Formula B can be substantially Formula A with $R^1$ a substituent on one or more ring atoms and independently being H, a halogen, Cl, F, Br, $NO_2$, $CH_3$, $CH_3CH_2$, or higher or lower substituted or unsubstituted straight chain or branched aliphatic (e.g., C1-C10), or cycle or heterocycle.

Formula C can be substantially Formula A or Formula B, and $R^1$ may be present or absent, and when present being a substituent on one or more ring atoms and independently being H, a halogen, Cl, F, Br, $NO_2$, $CH_3$, $CH_3CH_2$, or higher or lower substituted or unsubstituted straight chain or branched aliphatic (e.g., C1-C10), or cycle or heterocycle. $Y_2$-7 are independently selected from C, N, NH, N-alkyl, O, or S, and the ring formed therefrom may be cyclic or aromatic. $Y_7$ maybe present or absent so as to form a 5-membered ring.

Formula D can be substantially Formula A, Formula B or Formula D, and $R^1$ and $R^2$ may be present or absent, and when present each independently being a substituent on one or more ring atoms and independently being H, a halogen, Cl, F, Br, $NO_2$, $CH_3$, $CH_3CH_2$, or higher or lower substituted or unsubstituted straight chain or branched aliphatic (e.g., C1-C10), or cycle or heterocycle. $Y_2$-7 are independently selected from C, N, NH, N-alkyl, O, or S, and the ring formed therefrom may be cyclic or aromatic. $Y_7$ maybe present or absent so as to form a 5-membered ring.

Additionally, $Y_1$ or $R^2$ can be a mono-morpholine, bi-morpholine, or tri-morpholine, wherein each morpholine of such multi-morpholines are each independently described by Formulas A-D.

As used herein, the term "analog", "analogue," or "derivative" is meant to refer to a chemical compound or molecule made from a parent compound or molecule by one or more chemical reactions. As such, an analog can be a compound with a structure similar to that of Compounds I-34 or based on a scaffold of Formulas A-D, but differing from it in respect to certain components or structural makeup, which may have a similar or opposite action metabolically. Thiomorpholines and piperazines are specific examples of morpholine derivatives.

In one embodiment, the compounds of Formulas A-D can independently be derivatized/analogued by modifying the R groups independently from each other. That is, each R group on each molecule can be independently modified with respect to the other R groups on the same molecule. Any traditional modification for producing a derivative/analogue can be used. For example, the R groups of the derivatives/analogues can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like.

Additionally, the X groups of the morpholine can be independently selected from C, O, N, S, P, and like atoms, such as other hetero atoms.

As used herein, the term "hetero atoms" is meant to refer to atoms other than carbon atoms such as oxygen, nitrogen, sulfur, phosphorus, and the like. Usually, a heteroatom is multivalent so as to form at least two covalent bonds, which can be used in a linking group or other moiety.

As used herein, the term "aliphatic" is meant to refer to a hydrocarbyl moiety, such as an alkyl group, that can be straight or branched, saturated or unsaturated, and/or substituted or unsubstituted, which has twenty or less carbons in the backbone. An aliphatic group may comprise moieties that are linear, branched, cyclic and/or heterocyclic, and contain functional groups such as ethers, ketones, aldehydes, carboxylates, and the like. Exemplary aliphatic groups include but are not limited to substituted and/or unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, alkyl groups of higher number of carbons and the like, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl, and the like. The terms aliphatic or alkyl also encompasses alkenyl groups, such as vinyl, allyl, aralkyl and alkynyl groups.

Substitutions within an aliphatic group can include any atom or group that can be tolerated in the aliphatic moiety, including but not limited to halogens, sulfurs, thiols, thioethers, thioesters, amines (primary, secondary, or tertiary), amides, ethers, esters, alcohols, oxygen, and the like. The aliphatic groups can by way of example also comprise modifications such as azo groups, keto groups, aldehyde groups, carbonyl groups, carboxyl groups, nitro, nitroso or nitrile groups, heterocycles such as imidazole, hydrazino or hydroxylamino groups, isocyanate or cyanate groups, and sulfur containing groups such as sulfoxide, sulfone, sulfide, and disulfide. Additionally, the substitutions can be via single, double, or triple bonds, when relevant or possible.

Further, aliphatic groups may also contain hetero substitutions, which are substitutions of carbon atoms, by hetero atoms such as, for example, nitrogen, oxygen, phosphorous, or sulfur. As such, a linker comprised of a substituted aliphatic can have a backbone comprised of carbon, nitrogen, oxygen, sulfur, phosphorous, and/or the like. Heterocyclic substitutions refer to alkyl rings having one or more hetero atoms. Examples of heterocyclic moieties include but are not limited to morpholino, imidazole, and pyrrolidino.

Also, any cycloalkyl groups shown in Formulas A-D can be substituted with a aromatic group having about the same number of members in the ring so long as the molecule is still a morpholine.

As used herein, the term "aromatic" is meant to refer to molecule is one in which electrons are free to cycle around circular or cyclic arrangements of atoms, which are alternately singly and doubly bonded to one another. More properly, these bonds may be seen as a hybrid of a single bond and a double bond, each bond in the ring being identical to every other. Examples of aromatic compounds that can be present include benzene, benzyl, toluene, xylene, and the like. The aromatic compound can include hetero atoms so as to be a hetero aromatic such as pyridine, furan, tetrahydrofuran, and the like. Also, an aromatic can be a polycyclic aromatic such as naphthalene, anthracene, phenanthrene, polycyclic aromatic hydrocarbons, indole, quinoline, isoquinoline, and the like.

As used herein, the term "amine" is meant to refer to moieties that can be derived directly or indirectly from ammonia by replacing one, two, or three hydrogen atoms by other groups, such as, for example, alkyl groups. Primary amines have the general structures $RNH_2$ and secondary amines have the general structure $R_2NH$. The term amine includes, but is not limited to methylamine, ethylamine, propylamine, isopropylamine, aniline, cyclohexylamine, benzylamine, polycyclic amines, heteroatom substituted aryl and alkylamines, dimethylamine, diethylamine, diisopropylamine, dibutylamine, methylpropylamine, methylhexylamine, methylcyclopropylamine, ethylcylohexylamine, methylbenzylamine, methycyclohexylmethylamine, butylcyclohexylamine, morpholine, thiomorpholine, pyrrolidine, piperidine, 2,6-dimethylpiperidine, piperazine, and heteroatom substituted alkyl or aryl secondary amines.

As used herein, the term "halo" means fluoro, chloro, bromo, or iodo, preferably fluoro and chloro.

As used herein, the term "poly(amino acid)" or "polypeptide" is a polyamide formed from amino acids. Poly(amino acid)s will generally range from about 200-2,000 molecular weight or greater than about 2,000 molecular weight, or having no upper molecular weight limit, and normally being less than 10,000,000 and usually not more than about 600,000 daltons.

As used herein, the term "peptide" is meant to refer to any compound formed by the linkage of two or more amino acids by amide (peptide) bonds, usually a polymer of α-amino acids in which α-amino group of each amino acid residue (except the $NH_2$ terminus) is linked to the α-carboxyl group of the next residue in a linear chain. The terms "peptide," "polypeptide," and "poly(amino acid)" are used synonymously herein to refer to this class of compounds without restriction as to size. The largest members of this class are referred to as proteins.

Additionally, some of the compounds of the present invention can be prepared as racemic mixtures of isomers, mixtures of isomers, or optically isolated isomers. Compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", $4^{th}$ edition J. March, John Wiley and Sons, New York, 1992).

III. Therapeutic Methods

The compounds of the present invention can be used for the treatment, inhibition, and/or prevention of cancer in a subject. This can include lung cancer or other cancers. The ability of a compound of the present invention to inhibit CYP2A13 may provide for new therapeutic methods for cancer.

As used herein, the term "treating" or "treatment" of a disease, such as cancer, includes: (a) preventing the disease, i.e. causing the clinical symptoms of the disease not to develop in a mammal that may be exposed to or predisposed to the disease but does not yet experience or display symptoms of the disease; (b) inhibiting the disease, i.e., arresting or reducing the development of the disease or its clinical symptoms; or (c) relieving the disease, i.e., causing regression of the disease or its clinical symptoms. Inhibiting cancer can also include inhibiting cancer propagation. Prevention of cancer can include total prevention as well as a temporary prevention so as to delay onset. Inhibition and prevention can be useful for subjects that have been identified to be susceptible to cancer, such as a smoker.

In one embodiment, a compound of the present invention can be administered to a subject that is susceptible to or has cancer. As such, the treatment, inhibition, and/or prevention of cancers can be performed by administering to a subject in need thereof an effective amount of a compound as described herein. Optionally, the compound can be administered in combination with a pharmaceutically acceptable additive, carrier or excipient.

In one embodiment, a therapeutic method can include a method for inhibiting and/or preventing the growth of cancers. Such a method can include identifying a subject to have a malignant tumor or cancer (e.g., lung cancer), and then administering a compound of the present invention in an inhibitory or therapeutically effective amount or concentration.

The therapeutic methods can be used with one or more of the compounds described herein. Also, the compounds can be coadministered together or with other therapeutic compounds, such as other compounds that can be used in managing cancer. As such, the compounds of the present invention can be administered alone, in combination with each other, or they can be used in combination with other known compounds. For instance, the compounds can be used in conjunctive therapy with other known anti-angiogenic chemotherapeutic or antineoplastic agents (e.g., vinca alkaloids, antibiotics, antimetabolites, platinum coordination complexes, etc.). For instance, the compounds can be used in conjunctive therapy with a vinca alkaloid compound, such as vinblastine, vincristine, taxol, etc.; an antibiotic, such as adriamycin (doxorubicin), dactinomycin (actinomycin D), daunorubicin (daunomycin, rubidomycin), bleomycin, plicamycin (mithramycin) and mitomycin (mitomycin C), etc.; an antimetabolite, such as methotrexate, cytarabine (AraC), azauridine, azaribine, fluorodeoxyuridine, deoxycoformycin, mercaptopurine, etc.; or a platinum coordination complex, such as cisplatin (cis-DDP), carboplatin, etc. In addition, the compounds can be used in conjunctive therapy with other known anti-angiogenic chemotherapeutic or antineoplastic compounds.

As used herein, the term "coadministration" or "combination therapy" is used to describe a therapy in which at least two active compounds in effective amounts are used to treat lung tumors. Although the term coadministration preferably includes the administration of two active compounds to the patient at the same time, it is not necessary that the compounds be administered to the patient at the same time, although effective amounts of the individual compounds will be present in the patient at the same time.

IV. Pharmaceutical Compositions

Compounds according to the present invention may be used in pharmaceutical compositions having biological/pharmacological activity for the treatment of cancers by selectively inhibiting CYP2A13. These compositions comprise an effective amount of any one or more of the compounds disclosed herein, optionally in combination with a pharmaceutically acceptable additive, carrier, or excipient. Also, the compounds can be combined and/or prepared into pharmaceutically acceptable salts. The compounds may also be co-administered with other therapeutic agents. The effective amount can be a therapeutically effective amount of the compound sufficient for use in treating, inhibiting, and/or preventing cancer, such as lung cancers, as well as other cancers.

As used herein, the terms "an effective amount", "therapeutic effective amount", or "therapeutically effective amount" shall mean an amount or concentration of a compound according to the present invention which is effective within the context of its administration or use. Thus, the term "effective amount" is used throughout the specification to describe concentrations or amounts of compounds according to the present invention which may be used to produce a favorable change in the disease or condition treated, whether that change is a remission, a decrease in growth or size of cancer or a tumor, a favorable physiological result, a reduction in the growth or elaboration of a microbe, or the like, depending upon the disease or condition treated.

As used herein, the term "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

As used herein, the term "pharmaceutically acceptable acid addition salts" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Groups which form pharmaceutically acceptable acid addition salts include amines, hydrazines, amidines, guanidines, substituted aryl/heteroaryl and substituted alkyl groups that carry at least a nitrogen bearing substituent such as amino, uanidine, amidino, uanidine and the like.

The compounds of the present invention can be formulated into a pharmaceutically acceptable formulation. Such a composition can be useful to prevent, alleviate, eliminate, or delay the onset of breast and/or ovarian cancers, and thereby can be used as an inhibitor, prophylactic, or treatment for breast and/or ovarian cancers.

In embodiments of the present invention, the pharmaceutical composition comprises an active component and inactive components. The active components are compounds described herein and their derivatives/analogues. The inactive components are selected from the group consisting of excipients, carriers, solvents, diluents, stabilizers, enhancers, additives, adhesives, and combinations thereof.

The amount of the compound in a formulation can vary within the full range employed by those skilled in the art. Typically, the formulation will contain, on a weight percent basis, from about 0.01-99.99 weight percent of the compounds of the present invention based on the total formulation, with the balance being one or more suitable pharmaceutical excipients. Preferably, the compounds are present at a level of about 1-80 weight percent.

Pharmaceutical preparations include sterile aqueous or non-aqueous solutions, suspensions and emulsions. Examples of non-aqueous solvents are propylene glycol, polyethylene glycol, vegetable oil such as olive oil, injectable organic esters such as ethyloliate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, (such as those based on Ringer's dextrose), and the like. Preservatives and other additives may also be present such as, for example, antimicrobials, antioxidants, chelating agents and inert gases and the like. Those of skill in the art can readily determine the various parameters for preparing these pharmaceutical compositions without resort to undue experimentation.

Pharmacological compositions may be prepared from water-insoluble compounds, or salts thereof, such as aqueous base emulsions. In such embodiments, the pharmacological composition will typically contain a sufficient amount of pharmaceutically acceptable emulsifying agent to emulsify the desired amount of the pharmacological agent. Useful emulsifying agents include, but are not limited to, phosphatidyl cholines, lecithin, and the like.

Additionally, the compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate.

Furthermore, pharmacological agent compositions may, though not always, contain microbial preservatives. Microbial preservatives that may be employed include, but are not limited to, methylparaben, propylparaben, and benzyl alcohol.

The microbial preservative may be employed when the pharmacological agent formulation is placed in a vial designed for multi-dose use. Pharmacological agent compositions for use in practicing the subject methods may be lyophilized using techniques well known in the art.

The compositions may also include components, such as cyclodextrins, to enhance the solubility of one or more other components included in the compositions. Cyclodextrins are widely known in the literature to increase the solubility of poorly water-soluble pharmaceuticals or drugs and/or enhance pharmaceutical/drug stability and/or reduce unwanted side effects of pharmaceuticals/drugs. For example, steroids, which are hydrophobic, often exhibit an increase in water solubility of one order of magnitude or more in the presence of cyclodextrins. Any suitable cyclodextrin component may be employed in accordance with the present invention. The useful cyclodextrin components include, but are not limited to, those materials which are effective in increasing the apparent solubility, preferably water solubility, of poorly soluble active components and/or enhance the stability of the active components and/or reduce unwanted side effects of the active components. Examples of useful cyclodextrin components include, but are not limited to: β-cyclodextrin, derivatives of β-cyclodextrin, carboxymethyl-β-cyclodextrin, carboxymethyl-ethyl-β-cyclodextrin, diethyl-β-cyclodextrin, dimethyl-β-cyclodextrin, methyl-β-cyclodextrin, random methyl-β-cyclodextrin, glucosyl-β-cyclodextrin, maltosyl-β-cyclodextrin, hydroxyethyl-β- cyclodextrin, hydroxypropyl-β-cyclodextrin, sulfobutylether-β-cyclodextrin, and the like and mixtures thereof.

The specific cyclodextrin component selected should have properties acceptable for the desired application. The cyclodextrin component should have or exhibit reduced toxicity, particularly if the composition is to be exposed to sensitive body tissue, for example, eye tissue, etc. Very useful β-cyclodextrin components include β-cyclodextrin, derivatives of β-cyclodextrin and mixtures thereof. Particularly useful cyclodextrin components include sulfobutylether β-cyclodextrin, hydroxypropyl cyclodextrin and mixtures thereof. Sulfobutylether β-cyclodextrin is especially useful, for example, because of its substantially reduced toxicity.

The pharmaceutically acceptable excipients, such as vehicles, adjuvants, carriers or diluents, are readily available to the public. Examples of suitable excipients can include, but are not limited to, the following: acidulents, such as lactic acid, hydrochloric acid, and tartaric acid; solubilizing components, such as non-ionic, cationic, and anionic surfactants; absorbents, such as bentonite, cellulose, and kaolin; alkalizing components, such as diethanolamine, potassium citrate, and sodium bicarbonate; anticaking components, such as calcium phosphate tribasic, magnesium trisilicate, and talc; antimicrobial components, such as benzoic acid, sorbic acid, benzyl alcohol, benzethonium chloride, bronopol, alkyl parabens, cetrimide, phenol, phenylmercuric acetate, thimerosol, and phenoxyethanol; antioxidants, such as ascorbic acid, alpha tocopherol, propyl gallate, and sodium metabisulfite; binders, such as acacia, alginic acid, carboxymethyl cellulose, hydroxyethyl cellulose; dextrin, gelatin, guar gum, magnesium aluminum silicate, maltodextrin, povidone, starch, vegetable oil, and zein; buffering components, such as sodium phosphate, malic acid, and potassium citrate; chelating components, such as EDTA, malic acid, and maltol; coating components, such as adjunct sugar, cetyl alcohol, polyvinyl alcohol, carnauba wax, lactose maltitol, titanium dioxide; controlled release vehicles, such as microcrystalline wax, white wax, and yellow wax; desiccants, such as calcium sulfate; detergents, such as sodium lauryl sulfate; diluents, such as calcium phosphate, sorbitol, starch, talc, lactitol, polymethacrylates, sodium chloride, and glyceryl palmitostearate; disintegrants, such as colloidal silicon dioxide, croscarmellose sodium, magnesium aluminum silicate, potassium polacrilin, and sodium starch glycolate; dispersing components, such as poloxamer 386, and polyoxyethylene fatty esters (polysorbates); emollients, such as cetearyl alcohol, lanolin, mineral oil, petrolatum, cholesterol, isopropyl myristate, and lecithin; emulsifying components, such as anionic emulsifying wax, monoethanolamine, and medium chain triglycerides; flavoring components, such as ethyl maltol, ethyl vanillin, fumaric acid, malic acid, maltol, and menthol; humectants, such as glycerin, propylene glycol, sorbitol, and triacetin; lubricants, such as calcium stearate, canola oil, glyceryl palmitostearate, magnesium oxide, poloxymer, sodium benzoate, stearic acid, and zinc stearate; solvents, such as alcohols, benzyl phenylformate, vegetable oils, diethyl phthalate, ethyl oleate, glycerol, glycofurol, for indigo carmine, polyethylene glycol, for sunset yellow, for tartazine, triacetin; stabilizing components, such as cyclodextrins, albumin, xanthan gum; and tonicity components, such as glycerol, dextrose, potassium chloride, and sodium chloride; and mixture thereof. Excipients include those that alter the rate of absorption, bioavailability, or other pharmacokinetic properties of pharmaceuticals, dietary supplements, alternative medicines, or nutraceuticals.

Other examples of suitable excipients, binders and fillers are listed in Remington's Pharmaceutical Sciences, 18th Edition, ed. Alfonso Gennaro, Mack Publishing Co. Easton, Pa., 1995 and Handbook of Pharmaceutical Excipients, 3rd Edition, ed. Arthur H. Kibbe, American Pharmaceutical Association, Washington D.C. 2000, both of which are incorporated herein by reference.

In some embodiments, the compounds in the compositions may be present as a pharmaceutically acceptable salt. The term "pharmaceutically acceptable salts" includes salts of the composition, prepared, for example, with acids or bases, depending on the particular substituents found within the composition and the treatment modality desired. Pharmaceutically acceptable salts can be prepared as alkaline metal salts, such as lithium, sodium, or potassium salts; or as alkaline earth salts, such as beryllium, magnesium or calcium salts. Examples of suitable bases that may be used to form salts include ammonium, or mineral bases such as sodium hydroxide, lithium hydroxide, potassium hydroxide, calcium hydroxide, magnesium hydroxide, and the like. Examples of suitable acids that may be used to form salts include inorganic or mineral acids such as hydrochloric, hydrobromic, hydroiodic, hydrofluoric, nitric, carbonic, monohydrogencarbonic, phosphoric, monohydrogenphosphoric, dihydrogenphosphoric, sulfuric, monohydrogensulfuric, phosphorous acids and the like. Other suitable acids include organic acids, for example, acetic, propionic, isobutyric, maleic, malonic, benzoic, succinic, suberic, fumaric, mandelic, phthalic, benzenesulfonic, p-tolylsulfonic, citric, tartaric, methanesulfonic, glucuronic, galactunoric, salicylic, formic, naphthalene-2-sulfonic, and the like. Still other suitable acids include amino acids such as arginate, aspartate, glutamate, and the like.

In general, pharmaceutically acceptable carriers for are well-known to those of ordinary skill in the art. This carrier can be a solid or liquid and the type is generally chosen based on the type of administration being used. Suitable pharmaceutical carriers are, in particular, fillers, such as sugars, for example lactose, sucrose, mannitol or sorbitol, cellulose preparations and/or calcium phosphates, for example tricalcium phosphate or calcium hydrogen phosphate, furthermore, binders such as starch paste, using, for example, corn, wheat, rice or potato starch, gelatin, tragacanth, methylcellulose and/or polyvinylpyrrolidone, if desired, disintegrants, such as the abovementioned starches, furthermore carboxymethyl starch, crosslinked polyvinylpyrrolidone, agar, alginic acid or a salt thereof, such as sodium alginate; auxiliaries are primarily glidants, flow-regulators and lubricants, for example silicic acid, talc, stearic acid or salts thereof, such as magnesium or calcium stearate, and/or polyethylene glycol. Sugar-coated tablet cores are provided with suitable coatings which, if desired, are resistant to gastric juice, using, inter alia, concentrated sugar solutions which, if desired, contain gum arabic, talc, polyvinylpyrrolidone, polyethylene glycol and/or titanium dioxide, coating solutions in suitable organic solvents or solvent mixtures or, for the preparation of gastric juice-resistant coatings, solutions of suitable cellulose preparations, such as acetylcellulose phthalate or hydroxypropylmethylcellulose phthalate. Colorants or pigments, for example, to identify or to indicate different doses of active ingredient, may be added to the tablets or sugar-coated tablet coatings.

Additional pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Additional formulations for use in the present invention can be found in Remington's Pharmaceutical Sciences (Mack Publishing Company, Philadelphia, Pa., 17th ed. (1985)), which is incorporated herein by reference. Moreover, for a brief review of methods for drug delivery, see, Langer, Science 249:1527-1533 (1990), which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. Other examples of suitable pharmaceuticals are listed in 2000 Med Ad News 19:56-60 and The Physicians Desk Reference, 53rd edition, 792-796, Medical Economics Company (1999), both of which are incorporated herein by reference.

In general, compounds of this invention can be administered as pharmaceutical compositions by any one of the following routes: oral, systemic (e.g., transdermal, intranasal or by suppository), or parenteral (e.g., intramuscular, intravenous or subcutaneous) administration. One manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions. Another manner for administering compounds of this invention is inhalation.

Suitable preparations for parenteral administration are primarily aqueous solutions of an active ingredient in water-soluble form, for example a water-soluble salt, and furthermore suspensions of the active ingredient, such as appropriate oily injection suspensions, using suitable lipophilic solvents or vehicles, such as fatty oils, for example sesame oil, or synthetic fatty acid esters, for example ethyl oleate or triglycerides, or aqueous injection suspensions which contain viscosity-increasing substances, for example sodium carboxymethylcellulose, sorbitol and/or dextran, and, if necessary, also stabilizers.

Suitable rectally utilizable pharmaceutical preparations are, for example, suppositories, which consist of a combination of the active ingredient with a suppository base. Suitable suppository bases are, for example, natural or synthetic triglycerides, paraffin hydrocarbons, polyethylene glycols or higher alkanols. Furthermore, gelatin rectal capsules which contain a combination of the active ingredient with a base substance may also be used. Suitable base substances are, for example, liquid triglycerides, polyethylene glycols or paraffin hydrocarbons.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 (herein incorporated by reference) describes a pharmaceutical formulation having particles in the size range from 10 to 1,000 nm in which the active material is supported on a crosslinked matrix of macromolecules. U.S. Pat. No. 5,145,684 (herein incorporated by reference) describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

According to the methods of the present invention, the compositions of the invention can be administered by injection by gradual infusion over time or by any other medically acceptable mode. Any medically acceptable method may be used to administer the composition to the patient. The particular mode selected will depend of course, upon factors such as the particular drug selected, the severity of the state of the subject being treated, or the dosage required for therapeutic efficacy. The methods of this invention, generally speaking, may be practiced using any mode of administration that is medically acceptable, meaning any mode that produces effective levels of the active composition without causing clinically unacceptable adverse effects.

The administration may be localized (i.e., to a particular region, physiological system, tissue, organ, or cell type) or systemic. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be used for some treatments because of the convenience to the patient as well as the dosing schedule. Compositions suitable for oral administration may be presented as discrete units such as capsules, pills, cachettes, tables, or lozenges, each containing a predetermined amount of the active compound. Other oral compositions include suspensions in aqueous or non-aqueous liquids such as syrup, an elixir, or an emulsion.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Additionally, the morpholines or morpholine derivatives (e.g., thiomorpholines) can be formulated into cigarettes, cigars, or the like. This can allow the compound of the invention to be administered to a smoker so that the active compound is delivered while smoking. The compounds of the invention can be incorporated into tobacco products similar to the methods of incorporating other compounds into tobacco products.

The compounds can be formulated for parenteral administration by injection, e.g., by bolus injection or continuous infusion. Formulations for injection may be presented in unit dosage form, e.g., in ampules or in multidose containers, with an added preservative. The compositions may take such forms as suspensions, solutions or emulsions in oily or aqueous vehicles, and may contain formulator agents such as suspending, stabilizing and/or dispersing agents.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds can be encapsulated in a vehicle such as liposomes that facilitates transfer of the bioactive molecules into the targeted tissue, as described, for example, in U.S. Pat. No. 5,879,713 to Roth et al. and Woodle, et al., U.S. Pat. No. 5,013,556, the contents of which are hereby incorporated by reference. The compounds can be targeted by selecting an encapsulating medium of an appropriate size such that the medium delivers the molecules to a particular target. For example, encapsulating the compounds within microparticles, preferably biocompatible and/or biodegradable microparticles, which are appropriate sized to infiltrate, but remain trapped within, the capillary beds and alveoli of the lungs can be used for targeted delivery to these regions of the body following administration to a patient by infusion or injection.

Microparticles can be fabricated from different polymers using a variety of different methods known to those skilled in the art. The solvent evaporation technique is described, for example, in E. Mathiowitz, et al., J. Scanning Microscopy, 4, 329 (1990); L. R. Beck, et al., Fertil. Steril., 31, 545 (1979); and S. Benita, et al., J. Pharm. Sci., 73, 1721 (1984). The hot-melt microencapsulation technique is described by E. Mathiowitz, et al., Reactive Polymers, 6, 275 (1987). The spray drying technique is also well known to those of skill in the art. Spray drying involves dissolving a suitable polymer in an appropriate solvent. A known amount of the compound is suspended (insoluble drugs) or co-dissolved (soluble drugs) in the polymer solution. The solution or the dispersion is then spray-dried. Microparticles ranging between 1-10 microns are obtained with a morphology which depends on the type of polymer used.

Microparticles made of gel-type polymers, such as alginate, can be produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath to allow sufficient time for gelation to occur. Microparticle particle size is controlled by using various size extruders or varying either the nitrogen gas or polymer solution flow rates.

Particle size can be selected according to the method of delivery which is to be used, typically size IV injection, and where appropriate, entrapment at the site where release is desired.

In one embodiment, the liposome or microparticle has a diameter which is selected to lodge in particular regions of the body. For example, a microparticle selected to lodge in a capillary will typically have a diameter of between 10 and 100, more preferably between 10 and 25, and most preferably, between 15 and 20 microns. Numerous methods are known for preparing liposomes and microparticles of any particular size range. Synthetic methods for forming gel microparticles, or for forming microparticles from molten materials, are known, and include polymerization in emulsion, in sprayed drops, and in separated phases. For solid materials or pre-formed gels, known methods include wet or dry milling or grinding, pulverization, classification by air jet or sieve, and the like.

Embodiments may also include administration of at least one pharmacological agent using a pharmacological delivery device such as, but not limited to, pumps (implantable or external devices), epidural injectors, syringes or other injection apparatus, catheter and/or reservoir operatively associated with a catheter, injection etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert at least one pharmacological agent into the delivery device for administration of the pharmacological agent to a subject and include, but are not limited to, vials, ampules, tubes, capsules, bottles, syringes and bags.

Sterile injectable forms of the compositions of this invention may be aqueous or a substantially aliphatic suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Pharmacological agents may be delivered transdermally, by a topical route, formulated as applicator sticks, solutions, suspensions, emulsions, gels, creams, ointments, pastes, jellies, paints, powders, and aerosols. For example, embodiments may include a pharmacological agent formulation in the form of a discrete patch or film or plaster or the like adapted to remain in intimate contact with the epidermis of the recipient for a period of time. For example, such transdermal patches may include a base or matrix layer, e.g., polymeric layer, in which one or more pharmacological agent(s) are retained. The base or matrix layer may be operatively associated with a support or backing. Pharmacological agent formulations suitable for transdermal administration may also be delivered by iontophoresis and may take the form of an optionally buffered aqueous solution of the pharmacological agent compound. Suitable formulations may include citrate or bis/tris buffer (pH 6) or ethanol/water and contain a suitable amount of active ingredient. Topical application for the lower intestinal tract can be effected in a rectal suppository formulation (see above) or in a suitable enema formulation. Topically-transdermal patches may also be used.

For other topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Depending on the mode of administration, the pharmaceutical composition will preferably comprise from 0.05 to 99% by weight, more preferably from 0.1 to 70% by weight of the active ingredient, and, from 1 to 99.95% by weight, more preferably from 30 to 99.9% by weight of a pharmaceutically acceptable carrier, all percentages being based on the total composition.

The compositions of the present invention may be given in dosages, generally at the maximum amount while avoiding or minimizing any potentially detrimental side effects. The compositions can be administered in effective amounts, alone or in a cocktail with other compounds, for example, other compounds that can be used to treat and/or prevent breast and/or ovarian cancer. An effective amount is generally an amount sufficient to inhibit breast and/or ovarian cancer within the subject.

In one embodiment of the present invention, therapeutically effective amounts of compounds of the present invention may range from approximately 0.05 to 50 mg per kilogram body weight of the recipient per day; preferably about 0.01-25 mg/kg/day, more preferably from about 0.5 to 10 mg/kg/day. Thus, for administration to a 70 kg person, the dosage range would most preferably be about 35-70 mg per day.

In another embodiment of the present invention, dosages may be estimated based on the results of experimental models, optionally in combination with the results of assays of the present invention. Generally, daily oral doses of active compounds will be from about 0.01 mg/kg per day to 2000 mg/kg per day. Oral doses in the range of 10 to 500 mg/kg, in one or several administrations per day, may yield suitable results. In the event that the response of a particular subject is insufficient at such doses, even higher doses (or effective higher doses by a different, more localized delivery route) may be employed to the extent that patient tolerance permits. Multiple doses per day are also contemplated in some cases to achieve appropriate systemic levels of the composition. Dosage amount and interval may be adjusted individually to provide plasma levels of the active compound which are sufficient to maintain therapeutic effect. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

Although the exact dosage will be vary dependent upon the percent composition of the dosage of compounds of the present invention, in most cases some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro and in vivo data. Dosages necessary to achieve the MEC will depend on individual characteristics and route of administration. However, HPLC assays or bioassays can be used to determine plasma concentrations.

Use of a long-term release implant may be particularly suitable in some cases. "Long-term release," as used herein, means that the implant is constructed and arranged to deliver therapeutic levels of the composition for at least 30 or 45 days, and preferably at least 60 or 90 days, or even longer in some cases. Long-term release implants are well known to those of ordinary skill in the art, and include some of the release systems described above.

Any suitable dosage may be administered. The compound, the carrier, and the amount will vary widely depending on body weight, the severity of the condition being treated and other factors that can be readily evaluated by those of skill in the art. Generally a dosage of between about 1 mg per kg of body weight and about 100 mg per kg of body weight is suitable.

In pharmaceutical dosage forms, agents may be administered alone or with an appropriate association, as well as in combination, with other pharmaceutically active compounds. As used herein, "administered with" means that at least one pharmacological agent and at least one other adjuvant (including one or more other pharmacological agents) are administered at times sufficiently close that the results observed are indistinguishable from those achieved when one pharmacological agent and at least one other adjuvant (including one or more other pharmacological agents) are administered at the same point in time. The pharmacological agent and at least one other adjuvant may be administered simultaneously (i.e., concurrently) or sequentially. Simultaneous administration may be carried out by mixing at least one pharmacological agent and at least one other adjuvant prior to administration, or by administering the pharmacological agent and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that at least one pharmacological agent and at least one other adjuvant are administered at the same point in time or immediately following one another. In the latter case, the at least one pharmacological agent and at least one other adjuvant are administered at times sufficiently close that the results produced are synergistic and/or are indistinguishable from those achieved when the at least one pharmacological agent and at least one other adjuvant are administered at the same point in time. Alternatively, a pharmacological agent may be administered separately from the administration of an adjuvant, which may result in a synergistic effect or a separate effect. The methods and excipients described herein are merely exemplary and are in no way limiting.

Therapeutically effective dosages for the compounds described herein can be estimated initially from cell culture assays. For example, a dose can be formulated in animal models to achieve a circulating concentration range that includes the $IC_{50}$ as determined in cell culture (i.e., the concentration of test compound that is lethal to 50% of a cell culture), or the $IC_{100}$ as determined in cell culture (i.e., the concentration of compound that is lethal to 100% of a cell culture). Such information can be used to more accurately determine useful doses in humans. Initial dosages can also be estimated from in vivo data.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population), the $ED_{50}$ (the dose therapeutically effective in 50% of the population), and $EC_{50}$ (the excitatory concentration effective in 50% of the population). The dose ratio between toxic and therapeutic effect is the therapeutic index and can be expressed as the ratio between $LD_{50}$ and $ED_{50}$. Compounds which exhibit high therapeutic indices are candidates for further development. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: "The Pharmacological Basis of Therapeutics", Ch. 1, p. 1). Additionally, the $EC_{50}$ can be important to measure.

In one embodiment, a catheter is used to direct the composition directly to the location of the targeted tumor. As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

The exact formulation, route of administration and dosage for the pharmaceutical compositions of the present invention can be chosen by the individual physician in view of the patient's condition. (See e.g., et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $EC_{50}$, $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

EXPERIMENTAL

1.

To date, virtually all attempts to characterize full-length mammalian cytochromes P450 have been restricted by the production of only small (nanomolar) amounts of protein. However, truncation of the non-catalytic N-terminal transmembrane helix and addition of a C-terminal 4× histidine tag allow us to recombinantly produce tens of milligrams of highly purified modified CYP2A13 and CYP2A6 proteins per liter of E. coli culture. These engineered versions of the proteins (CYP2A13dH and CYP2A6dH are not shown) are fully functional in both binding ligands and metabolism of substrates. Protein expression in E. coli is initiated with the addition of IPTG to media supplemented with the heme precursor aminolevulinic acid. After 48-72 hours this expression system yields approximately 500-1300 nmol (27-71 mg) of CYP2A13dH or CYP2A6dH per liter of bacterial culture. Briefly, P450 proteins are liberated from E. coli membranes using a specialized detergent and high salt conditions and subsequently purified using metal-affinity and carboxymethyl-sepharose (CM-sepharose) affinity chromatography. Overall purification yield is up to 14 mg of highly purified protein per liter of E. coli culture.

Cytochrome P4502A13dH was expressed and purified as previously described (J. Biol. Chem. (2007), 282(23)17306-17313). Briefly, CYP2A13 was solubilized from the membrane using 4.8 mM Cymal-5 detergent (Anatrace, Maumee, Ohio) and 0.3M NaCl followed by ultracentrifugation at 30,000 rpm for 60 minutes. The solubilized protein was applied to $Ni^{2+}$-agarose resin (Qiagen, Valencia, Calif.) and after extensive washing with Buffer A (0.1M potassium phosphate, pH 7.4, 20% glycerol, 0.2M sodium chloride, 4.8 mM cymal, 8 mM histidine), the protein was eluted using Buffer B (Buffer A containing 2 mM EDTA and 80 mM histidine). The fractions containing protein with absorbance at 415 nm were pooled, diluted 5-fold with Buffer C (5 mM potassium phosphate, pH 7.4, 20% glycerol, 4.8 mM Cymal-5), and loaded onto HiTrap CM-FF column. The column was washed extensively with Buffer C without the detergent. Purified CYP2A13 was eluted using Buffer C with 50 mM potassium phosphate and 500 mM NaCl. An average yield of 14 mgs of CYP2A13 was obtained per litre of E. coli culture. Cytochrome P4502A6dH was similarly prepared.

2.

The UV/visible spectra of purified CYP2A13dH and CYP2A6dH have a Soret peak at 418 nm, indicative of a low-spin, six-coordinate configuration of the heme iron bound to an active site water molecule (FIG. 1A). When ligands bind in the active site they frequently displace the water from the iron, resulting in a shift to five-coordinate, high spin iron with a maximal absorbance ~395 nm. For cytochrome P450 enzymes, one often records the spectrum shift that occurs as protein is titrated with ligand to determine ligand affinity ($k_d$ values) (FIG. 1B).

In order to convert this assay to HTS mode, absorbance was measured at six wavelengths spanning the wavelength range of the spectral shift to verify that the same shifts were observed upon ligand binding in the HTS assay environment (FIG. 2). Because these initial experiments did exhibit the spectral shift as expected and because reading six wavelengths for each well is incredibly time-intensive, the assay was optimized to read only absorbance at the maximum (395 nm) and the minimum (418 nm) for each compound and compare the resulting difference in absorbance to that observed for PEITC binding (positive control). Compounds are screened in 384 well plates using a plate absorbance reader.

A spectral shift assay reflecting interactions of compounds with CYP2A13 was adapted to HTS format for screening compounds. Each 384-well screening plate contained 320 compounds (20 uM in 0.71% DMSO) and a set of standards comprising 32 wells: 16-wells each of 0.71% DMSO (Negative control), and 16-wells of Positive control (30 μM phenethylisothiocyanate or PEITC). Purified CYP2A13 (3 uM) was added to all the wells of the assay plates and the protein/compound mixtures were allowed to equilibrate at room temperature for 5 minutes. The plates were read on SpectraMax (Molecular Devices, CA) at 385 nm and 420 nm. The raw data were directly uploaded into spreadsheets that enabled hit identification based on the difference in raw absorbance values at 385 nm and 420 nm.

In an initial survey of 1760 compounds, we had a hit rate of ~2.5%. This hit rate is very high for most HTS assays, but may reflect the nature of the target. Cytochrome P450 enzymes are promiscuous by design and might be expected to bind a higher number of library compounds than most proteins.

However, survey of the same 1760 compounds with CYP2A6 yielded a hit rate of only 0.28%. This suggested a substantial number of compounds that are selective for CYP2A13 binding.

The compounds that induced spectral shifts close to that of the positive control (PEITC) were validated in the spectral shift assay using the low throughput cuvette method. CYP2A13 protein samples were diluted to a concentration of 1 µM in 100 mM potassium phosphate buffer (pH 7.4) and were divided equally between reference and sample 1 mL quartz cuvettes. Concentrated compound stocks were prepared in 100% DMSO and the sample baseline was taken from 300-500 nm before beginning the titration. Substrate was added to the sample cuvette, mixed, and allowed to equilibrate for 2 minutes. An equal amount of ethanol was added to the reference cuvette for every addition of compound stock to the sample. The total amount of ethanol was kept less than 2% for each titration. After each coumarin addition, difference spectra were recorded from 300-500 nm and the change maximum (~420 nm) to the minimum (~385 nm) was determined. Graphpad Prism 4 (Graphpad Software, San Diego, Calif.) was used to determine the $K_s$ and $\Delta A_{max}$ with nonlinear least-squares regression fitting to the equation:

$$\Delta A = \frac{\Delta A_{max}}{2P}\left[P + S + K_s - \sqrt{(P + S + K_s)^2 - 4PS}\right].$$

3.

In order to verify that the two-wavelength HTS assay is reliable for detecting true hits for CYP2A13 binding and not false positives, a set of 10 compounds identified as hits from the initial 1760-compound survey were further investigated. CYP2A13 was titrated with these compounds one at a time in a full spectral assay. Most of these compounds did bind to CYP2A13, but several had intrinsic absorbance in the 395 nm range that precluded definitive spectral analysis. Of the ten, 50% were validated as true ligands of CYP2A13. One of these compounds, 4-(2-chloro-6-fluorobenzyl)morpholine (shown below), has a $k_d$ of approximately 5.8 µM with CYP2A13, but caused absolutely no spectral shift with CYP2A6 (FIGS. 3A-3C).

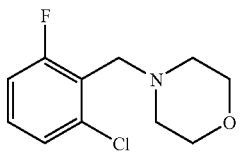

4-(2-chloro-6-fuorobenzyl)morpholine

4.

Identification of one CYP2A13-selective scaffold and subsequent analog studies. Subsequent analysis of our small compound survey revealed that two additional morpholine structures (e.g., 4-(2-methylbenzyl)morpholine and 4-(2-chlorobenzyl)morpholine) were also identified as hits. These compounds were further characterized for their binding to CYP2A13 and CYP2A6. These two additional morpholines bound to CYP2A13 with initial Kd values of 4 µM and 1.8 µM, but gave no spectral shift with CYP2A6. Using multiple titrations including that shown in FIGS. 4A-4C, 4-(2-methylbenzyl)morpholine was determined to have an average Kd of 19.3, and no substantially binding for CYP2A6dH. Using multiple titrations including that shown in FIGS. 5A-5C, 4-(2-chlorobenzyl)morpholine was determined to have an average Kd for CYP2A13 of 7.3 µM, and no substantially binding for CYP2A6.

4-(2-methylbenzyl)morpholine    4-(2-chlorobenzyl)morpholine

Further validation of 4-(2-chlorobenzyl)morpholine, 4-(2-chloro-6-fluorobenzyl)morpholine, 4-(2-methylbenzyl)morpholine, and other morpholine derivatives shown in Table 1 were performed. The validation provided the average Kd for CYP2A13, CYP2A6, and selectivity by (CYP2A6 Kd)/(CYP2A13 Kd). For selectivity, higher numbers are more selective.

TABLE 1

| Compound | Structure | 2A13 Av. $K_d$ (µM) | 2A6 Av. $K_d$ (µM) | Selectivity 2A6 $K_d$/ 2A13 $K_d$ |
|---|---|---|---|---|
| 4-(2-chlorobenzyl)morpholine Compound 1 | 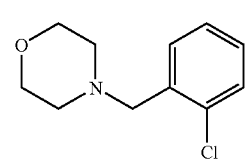 [SMILES: Clc1ccccc1CN1CCOCC1] | 7.3 | No binding | high |
| 4-(2-chloro-6-fluorobenzyl)morpholine Compound 2 | 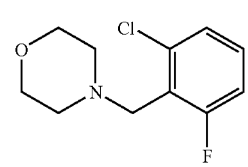 [SMILES: Fc1cccc(Cl)c1CN1CCOCC1] | 5.8 | No binding | high |

TABLE 1-continued

| Compound | Structure | 2A13 Av. $K_d$ (μM) | 2A6 Av. $K_d$ (μM) | Selectivity 2A6 $K_d$/ 2A13 $K_d$ |
|---|---|---|---|---|
| 4-(2-methylbenzyl)morpholine Compound 3 | 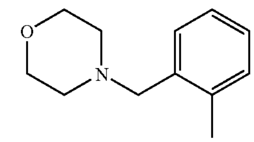 | 19.3 | No binding | high |
| 4-(2-bromobenzyl)morpholine Compound 4 | 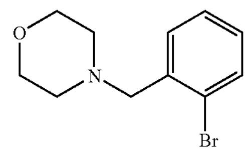 | 7 | No binding | high |
| 4-(2-fluorobenzyl)morpholine Compound 5 | 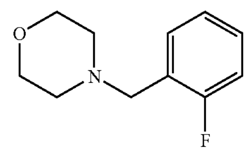 | 72.5 | No binding | high |
| 4-(2-chlorobenzyl)thiomorpholine Compound 6 | 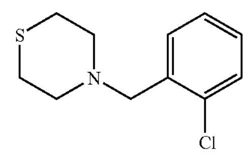 [SMILES: Clc1ccccc1CN1CCSCC1] | 10 | 155 | 15.5 |
| 4-(2,3-dichlorobenzyl)morpholine Compound 7 | 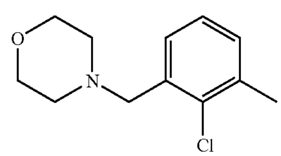 | 28.5 | 788 | 27 |
| 4-(2,6-dichlorobenzyl)morpholine Compound 8 | 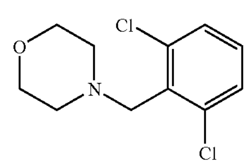 [SMILES: Clc1cccc(Cl)c1CN1CCOCC1] | 1.9 | 553 | 291 |
| 4-(2,4-dichlorobenzyl)morpholine Compound 9 | 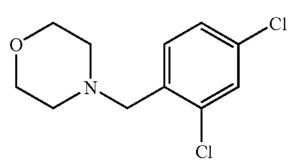 [SMILES: Clc1ccc(CN2CCOCC2)c(Cl)c1] | 35 | 198.2 | 5.66 |
| 4-(2,3-dichlorobenzyl)-1,6-dimethylmorpholine Compound 10 | 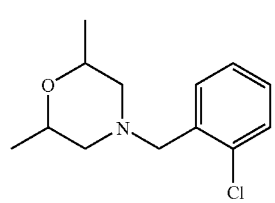 [SMILES: CC1CN(Cc2ccccc2Cl)CC(C)O1] | 37.7 | >486 | 12.9 |

Additional morpholine analogs that may be more selective for CYP2A13 over CYP2A6 in accordance with the present invention are shown in Table 2. These compounds are currently being synthesized and evaluated to explore the effects of further scaffold variation on the affinity and selectivity for human CYP2A enzymes.

TABLE 2

1,3,4,6,11,11a-hexahydro-[1,4]oxazino[4,3-b]isoquinoline (Compound 11)

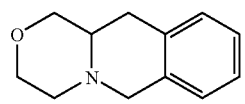 [SMILES: c1ccc2c(c1)CC1COCCN1C2]

TABLE 2-continued

| | |
|---|---|
| 1-(2,6-dichlorobenzyl)-4-methylpiperazine (Compound 12 is a morpholine derivative) | 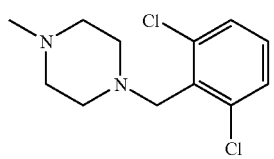 [SMILES: CN1CCN(Cc2c(Cl)cccc2Cl)CC1] |
| 1-(2-chlorobenzyl)-4-methyl-piperazine (Compound 13 is a morpholine derivative) | 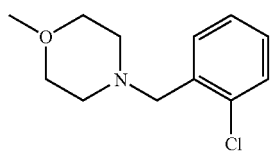 |
| 4-(1-(2-chlorophenyl)ethyl)morpholine (Compound 14) | 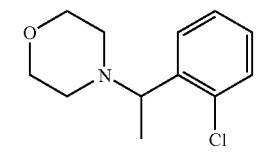 |
| 4-(2,6-dichlorobenzyl)-1-methylpiperazine 1-oxide (Compound 15 is a morpholine derivative) | 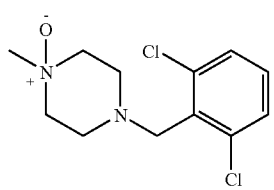 |
| 4-(2,6-dichlorobenzyl)-3-methylmorpholine (Compound 16) | 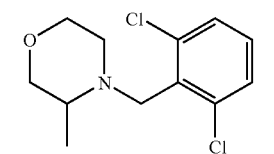 |
| 4-(2,6-diethylbenzyl)morpholine (Compound 17) | 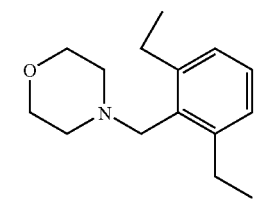 [SMILES: CCc1cccc(CC)c1CN1CCOCC1] |
| 4-(2-chlorophenethyl)morpholine (Compound 18) | 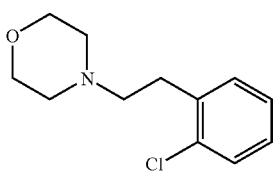 [SMILES: Clc1ccccc1CCN1CCOCC1] |
| 4-(2-ethylbenzyl)morpholine (Compound 19) | 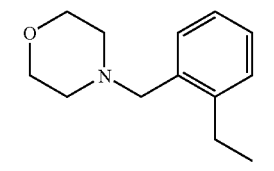 |
| 4-(2-isopropylbenzyl)morpholine (Compound 20) | 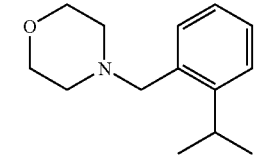 [SMILES: CC(C)c1ccccc1CN1CCOCC1] |

TABLE 2-continued

| | |
|---|---|
| 4-(2-propylbenzyl)morpholine (Compound 21) | 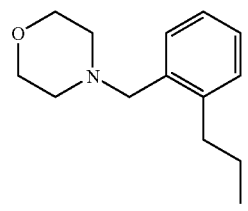 [SMILES: CCCc1ccccc1CN1CCOCC1] |
| 4-(3-(2-chlorophenyl)propyl)morpholine (Compound 22) | 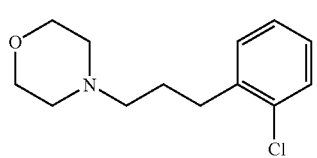 [SMILES: Clc1ccccc1CCCN1CCOCC1] |
| 4-(3-chlorobenzyl)morpholine (Compound 23) | 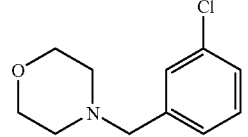 |
| 4-(naphthalen-1-ylmethyl)morpholine (Compound 24) | 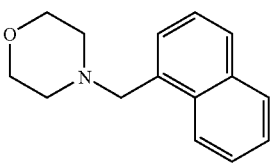 [SMILES: c1ccc2c(CN3CCOCC3)cccc2c1] |
| 4-benzylmorpholine (Compound 25) | 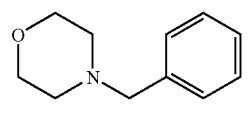 [SMILES: c1ccc(CN2CCOCC2)cc1] |
| 4-benzyl-3,5-dimethyl-morpholine (Compound 26) | 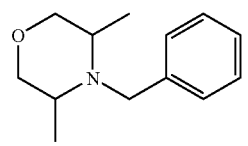 |
| 4-(4-chlorobenzyl)morpholine (Compound 27) | 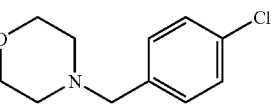 |
| 4-(2-chlorobenzyl)-3,5-dimethylmorpholine (Compound 28) | 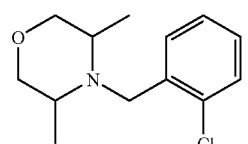 |
| 4-(2-chlorobenzyl)-3-methyl-morpholine (Compound 29) | 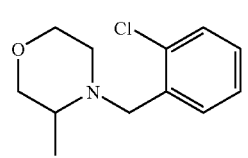 |
| 4-(2-benzylbenzyl)morpholine (Compound 30) | 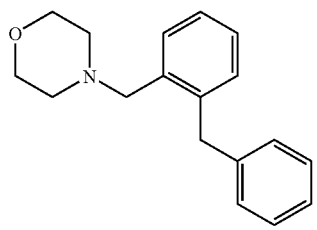 [SMILES: c1ccc(Cc2ccccc2CN2CCOCC2)cc1] |

TABLE 2-continued

| | |
|---|---|
| 4-(2-adamantyl)morpholine hydrochloride 2A13 Kd = 28.75 (Compound 31) | 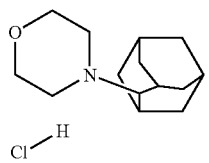 |
| 4-(3-chlorobenzyl)morpholine (Compound 32) | 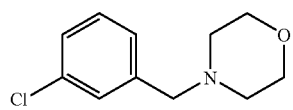 [SMILES: Clc1cccc(CN2CCOCC2)c1] |
| 4-(phenylacetyl)morpholine (Compound 33) | 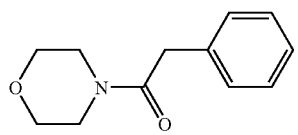 [SMILES: O=C(Cc1ccccc1)N1CCOCC1] |
| 4-(2-adamantyl)-2,6-dimethyl-morpholine (Compound 34) | 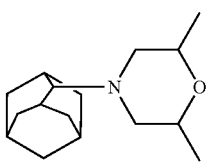 |

6.

Enzyme inhibition studies can be performed to further validate morpholine derivatives. Assays were focused on ligand binding because catalytic activity requires not only the cytochrome P450 protein, but also two additional accessory proteins, NADPH cytochrome P450 reductase and cytochrome b5. To evaluate the ability of selective ligand-binding hits to selectively inhibit enzymatic turnover, a coumarin hydroxylation assay can be used for both CYP2A13 and CYP2A6. This relatively simple assay produces a fluorescent metabolite, 7-hydroxycoumarin, that is easily detected. Briefly, the reconstituted system contains purified P450 protein, NADPH-cytochrome P450 reductase, cytochrome b5, coumarin, and NADPH in a potassium buffer. After incubation at 37° C. for 10 min, the reaction is stopped by the addition of trichloroacetic acid. The final 7-hydroxycoumarin metabolite is detected by fluorescence using an excitation wavelength of 368 nm and an emission wavelength of 453 nm. This assay can be adapted to a high throughput assay for 384-well plates using a Bio-tek FL600 for fluorescent metabolite detection. Initially, compounds can be selected by their ability to reduce 7-hydroxycoumarin generation from coumarin over time, compared to assays with no inhibitor. Known inhibitors can be used as controls. To determine KI values, formation of the metabolites can be measured in the presence of increasing concentrations of the inhibitor. The substrate concentrations can range from ½ Km to twice the Km. At each substrate concentration, metabolite formation can be monitored in the absence and presence of the inhibitors. KI values can be generated by Dixon plot analysis and used to select the best selective inhibitors of CYP2A13 over CYP2A6.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references (e.g., journal articles, published patent applications, patents, and the like) identified herein are incorporated herein by specific reference in their entirety.

The invention claimed is:

1. A method for inhibiting activity of cytochrome P450 2A13 in a subject comprising administering to a subject who is a smoker or who has been exposed to second hand smoke a therapeutically effective amount of a morpholine compound so as to inhibit activity of cytochrome P450 2A13 and the subsequent formation of cancerous metabolites of 4-(methylnitrosoamino)-1-(3-pyridyl)-1-butanone (NNK) by cytochrome P450 2A13, wherein said morpholine compound comprises 4-(2-chlorobenzyl)morpholine, 4-(2-chloro-6-fluorobenzyl) morpholine, 4-(2-methylbenzyl)morpholine, 4-(2-bromobenzyl)morpholine, 4-(2-chlorobenzyl) thiomorpholine, 4-(2,3-dichlorobenzyl) morpholine, 4-(2,6-dichlorobenzyl) morpholine, or 4-(2,4-dichlorobenzyl) morpholine.

2. The method of claim 1, wherein the morpholine compound is substantially more selective for interacting with the cytochrome P450 2A13 over the cytochrome P450 2A6.

3. A method of inhibiting formation of cancerous lung cells in a subject comprising administering to a subject who is a smoker or who has been exposed to second hand smoke a therapeutically effective amount of a morpholine compound so as to inhibit activity of cytochrome P450 2A13 and the subsequent formation of cancerous lung cells due to activity of cancerous NNK metabolites formed by cytochrome P450 2A13, wherein said morpholine compound comprises 4-(2-chlorobenzyl)morpholine, 4-(2-chloro-6-fluorobenzyl) morpholine, 4-(2-methylbenzyl)morpholine, 4-(2-bromobenzyl) morpholine, 4-(2-chlorobenzyl) thiomorpholine, 4-(2,3-dichlorobenzyl) morpholine, 4-(2,6-dichlorobenzyl) morpholine, or 4-(2,4-dichlorobenzyl) morpholine.

4. A morpholine compound having the structure

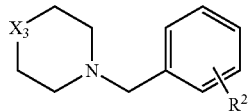

wherein,
$X_3$ is O or S; and
$R^2$ is a substituent on one or more ring atoms and is independently a halogen or $CH_3$, and further wherein said compound comprises 4-(2-chloro-6-fluorobenzyl) morpholine, 4-(2,3-dichlorobenzyl) morpholine, 4-(2,6-dichlorobenzyl) morpholine, or 4-(2,4-dichlorobenzyl) morpholine.

5. A pharmaceutical composition comprising the morpholine compound of claim 4 and a pharmaceutically acceptable carrier.

* * * * *